US008574236B2

(12) United States Patent
Sawatari et al.

(10) Patent No.: US 8,574,236 B2
(45) Date of Patent: Nov. 5, 2013

(54) METHOD FOR PREPARING RECIPIENT SITE AND IMPLANTING ALLOGENIC BONE GRAFT

(76) Inventors: Yoh Sawatari, Miami, FL (US); Michael Peleg, Miami, FL (US)

(*) Notice: Subject to any disclaimer, the term of this patent is extended or adjusted under 35 U.S.C. 154(b) by 264 days.

(21) Appl. No.: 12/920,633

(22) PCT Filed: Feb. 20, 2009

(86) PCT No.: PCT/US2009/034617
§ 371 (c)(1),
(2), (4) Date: Sep. 2, 2010

(87) PCT Pub. No.: WO2009/117208
PCT Pub. Date: Sep. 24, 2009

(65) Prior Publication Data
US 2011/0034931 A1    Feb. 10, 2011

Related U.S. Application Data

(60) Provisional application No. 61/064,651, filed on Mar. 18, 2008.

(51) Int. Cl.
*A61B 17/16* (2006.01)

(52) U.S. Cl.
USPC ............................................. 606/80; 433/215

(58) Field of Classification Search
USPC ................... 606/104, 300–331, 79–80, 96; 623/16.11, 23.51, 23.6–23.63, 17.17; 433/72, 50, 75, 143–144, 165–166, 433/176, 215
See application file for complete search history.

(56) References Cited

U.S. PATENT DOCUMENTS

| 4,830,615 | A | * | 5/1989 | Goldstein et al. | 433/166 |
|---|---|---|---|---|---|
| 5,439,381 | A | * | 8/1995 | Cohen | 433/173 |
| 5,967,777 | A | * | 10/1999 | Klein et al. | 433/75 |
| 6,325,627 | B1 | | 12/2001 | Ashman | |
| 6,332,779 | B1 | | 12/2001 | Boyce et al. | |
| 6,343,931 | B1 | * | 2/2002 | Regni, Jr. | 433/175 |
| 6,511,509 | B1 | * | 1/2003 | Ford et al. | 623/23.5 |
| 6,537,070 | B1 | | 3/2003 | Stucki-McCormick | |

(Continued)

FOREIGN PATENT DOCUMENTS

WO    WO 99/26540    6/1999

OTHER PUBLICATIONS

International Search Report for PCT/US2009/034617, mailed Apr. 10, 2009.

(Continued)

*Primary Examiner* — Todd Manahan
*Assistant Examiner* — Marcela I Shirsat
(74) *Attorney, Agent, or Firm* — Robert M. Downey, P.A.

(57) ABSTRACT

A method of fixating allogeneic bone to an area of deficient bone in the jaws comprising: exposing the area of deficient bone by incising and retracting soft tissue; selecting a drill bit having a diameter corresponding to the area of deficient bone to receive donor bone; contacting the selected drill bit with the exposed deficient bone to form a generally cylindrical seat for receiving the donor bone; selecting a section of donor bone having a generally cylindrical shape and circular cross-section corresponding to said formed seat; fixating the donor bone to the formed seat with at least one screw; and closing the soft tissue to cover the previously exposed deficient bone.

5 Claims, 3 Drawing Sheets

(56) References Cited

U.S. PATENT DOCUMENTS

| | | | |
|---|---|---|---|
| 6,899,715 B1 | 5/2005 | Beaty | |
| 7,021,933 B2* | 4/2006 | Caldwell | 433/165 |
| 7,241,144 B2 | 7/2007 | Nilo et al. | |
| 7,247,020 B2 | 7/2007 | Takahashi et al. | |
| 2004/0219479 A1* | 11/2004 | Malin et al. | 433/75 |
| 2005/0008990 A1* | 1/2005 | Ganz et al. | 433/215 |

OTHER PUBLICATIONS

McAllister et al., "Bone Augmentation Techniques", *J. Periodontol*, 2007, vol. 78, pp. 377-396.

Block et al., "Human Mineralized Bone in Extraction Sites Before Implants", *JADA*, Dec. 2002, vol. 133, pp. 1631-1638.

Keith et al., Clinical and Histologic Evaluation of a Mineralized Block Allograft: Results from the Developmental Period, *The International Journal of Periodontics and Restorative Dentistry*, Apr. 2006, vol. 26, pp. 321-327.

International Preliminary Report on Patentability and Written Opinion for PCT/US2009/034617, dated Sep. 30, 2010, 6 pages.

* cited by examiner

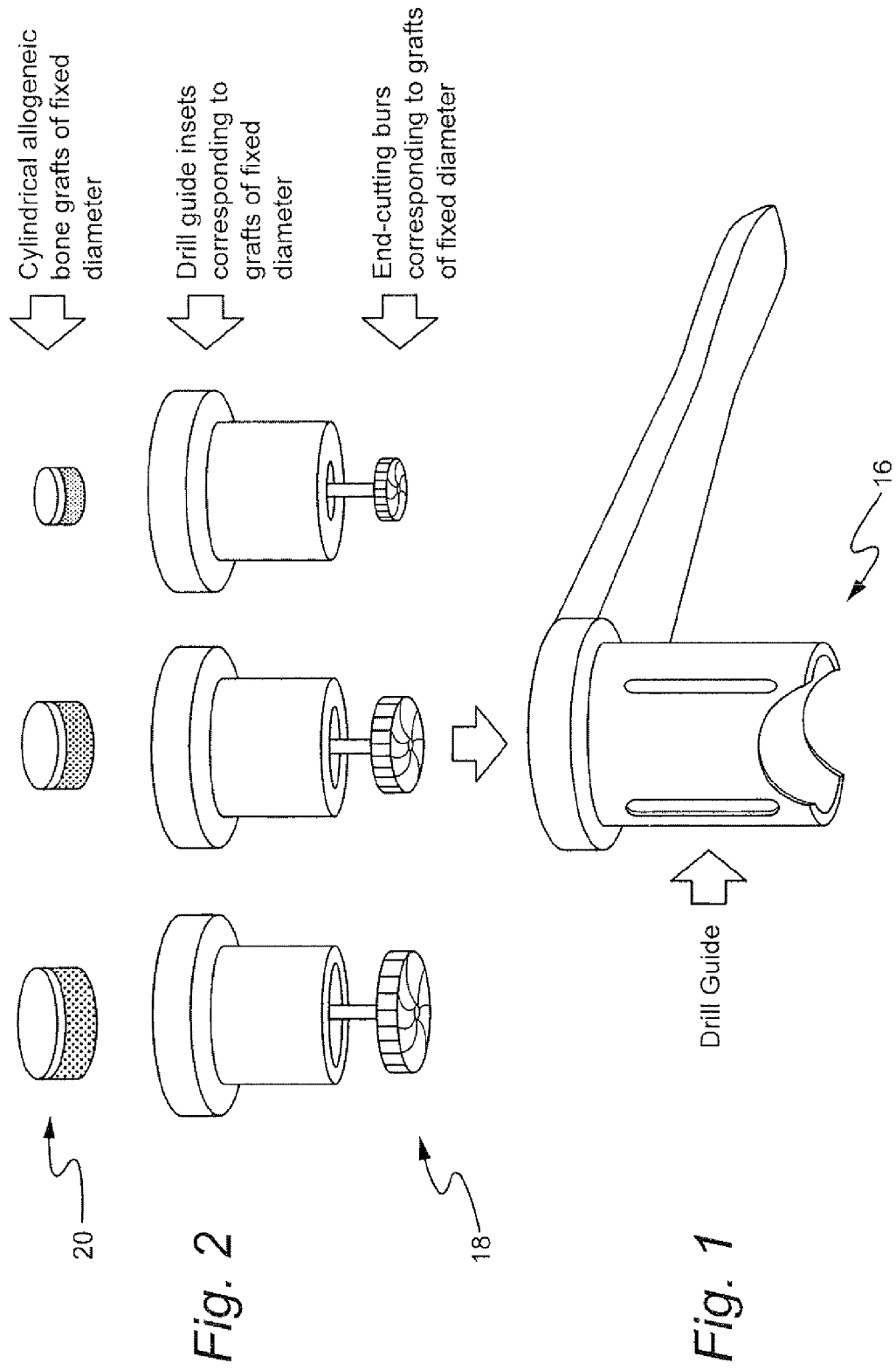

METHOD FOR PREPARING RECIPIENT SITE AND IMPLANTING ALLOGENIC BONE GRAFT

CROSS-REFERENCE TO RELATED APPLICATION

This application is the U.S. national phase of International Application No. PCT/US2009/034617 filed Feb. 20, 2009 which designated the U.S. and claims priority to U.S. Provisional Application No. 61/064,651 filed Mar. 18, 2008, the entire content of each of which are hereby incorporated by reference.

BACKGROUND OF THE INVENTION

The use of allogeneic grafting has become a standard methodology to increase bone volume in deficient areas of the maxilla and mandible. The purpose of this grafting procedure is to prepare the patient for the eventual restoration of the patient's function and esthetics with dental implants.

Conventionally, this procedure involves the surgical exposure of an area of deficient bone in the jaws, removal of a section of freeze dried iliac crest from a tissue bank, contouring the section from the iliac crest to follow the anatomical curvature of the target area of the jaw in which it is to be implanted and adapting the section of iliac crest to passively rest on the jaw with maximum contact with the existing bone matter. The section of allogeneic bone is then fixated to the deficient jaw for approximately four months to allow fusion of the allogeneic bone to the jaw and eventual replacement with autologous bone.

As described, the process is routine yet difficult. The most time consuming and critical aspect of the procedure involves the adaptation of the section of iliac crest to a deficient mandible. If there is poor adaptation, insufficient area contact, and/or a lack of stability at the time of fixation between the graft and the recipient jaw, the graft will fail to fuse and the patient will not receive any benefit from the graft procedure. Conventionally, the process which is utilized in the operating room or clinic involves the use of several different carbide burs to contour the surface which interfaces with the native jaw. Thus, once the surgical exposure is completed, the surgeon visualizes the recipient's site and through memory and repetitive test insert procedures, the surgeon will endeavor to produce the negative equivalent of the recipient site jaw contour in the allogeneic section. More specifically, the section of iliac crest is stabilized by the surgeon's hand or with an instrument while a rotary instrument on a handpiece is used to remove minimal amounts of bone to follow given contours of the jaw.

BRIEF DESCRIPTION OF THE INVENTION

To address the inherent difficulty in shaping or sculpting the section of iliac crest to approximate the shape of the recipient site, the invention proposes an allogeneic bone grafting procedure wherein the recipient site in the native jaw is manipulated rather than contouring the section of allogeneic bone.

Thus, the invention is embodied in a method of fixating allogeneic bone to an area of deficient bone in the jaws comprising: exposing the area of deficient bone by incising and retracting soft tissue; selecting a drill bit having a diameter corresponding to the area of deficient bone to receive donor bone; contacting the selected drill bit with a side of the exposed deficient bone to form a generally cylindrical seat transversely into the side of the deficient bone for receiving the donor bone; selecting a section of donor bone having a generally cylindrical shape and circular cross-section corresponding to said formed seat with at least one screw; and closing soft tissue to cover the previously exposed deficient bone.

BRIEF DESCRIPTION OF THE DRAWINGS

These and other objects and advantages of this invention, will be more completely understood and appreciated by careful study of the following more detailed description of the presently preferred exemplary embodiments of the invention taken in conjunction with the accompanying drawings, in which:

FIG. 1 is a schematic perspective view of a drill guide that may be provided in an example embodiment of the invention for aligning a drill guide insert with a target area of natural jaw;

FIG. 2 is a schematic illustration of drill guide inserts corresponding to grafts of predetermined fixed diameter for manipulating the recipient site to conform to the size of bone graft to be implanted;

DETAILED DESCRIPTION OF THE INVENTION

Figure 3:
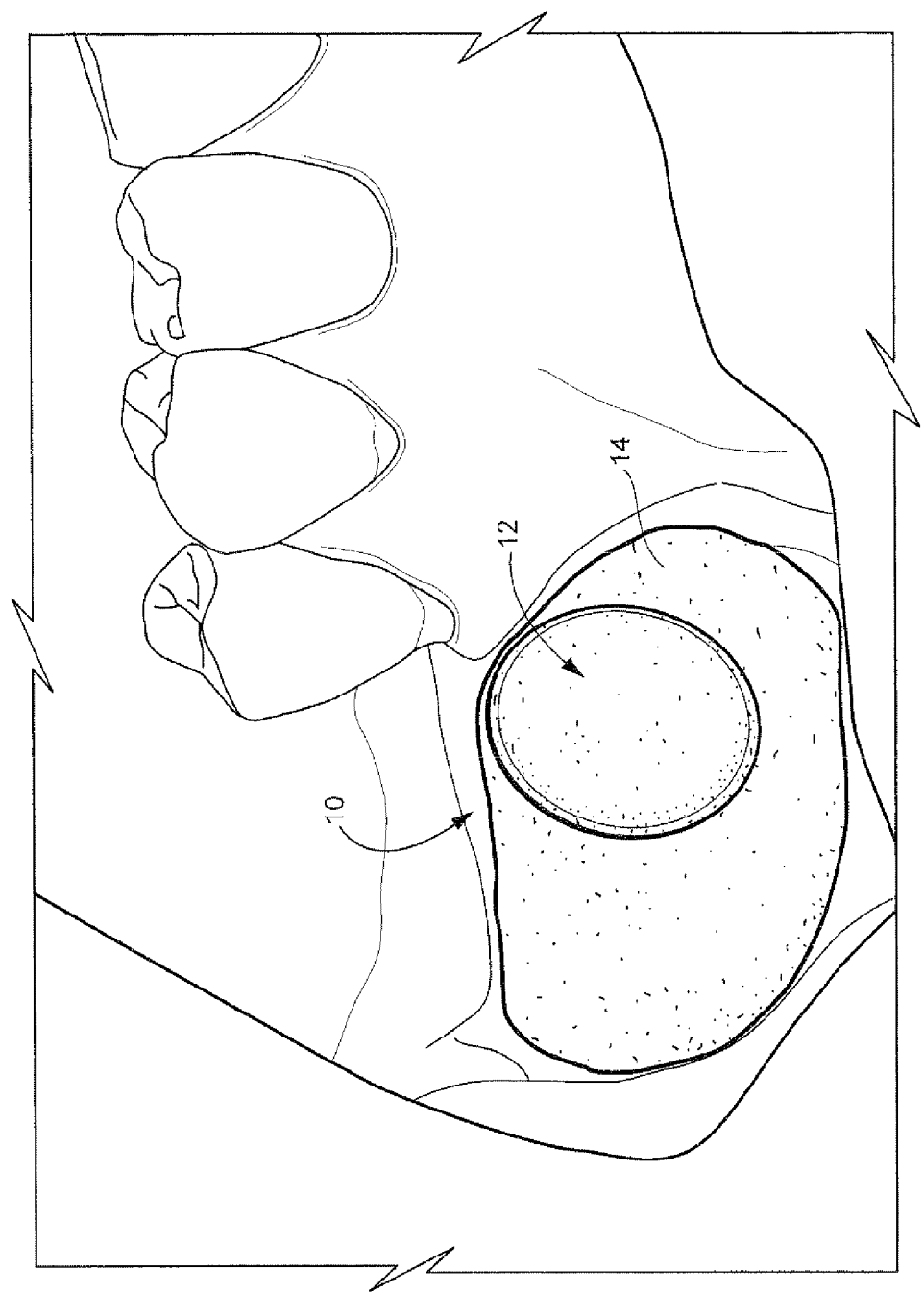
FIG. 3 is a schematic perspective view of an example recipient site having a transversely formed seat manipulated to have a shape corresponding to that of the allogeneic bone section.

To address difficulties of contouring a section of iliac bone for placement in a recipient site, in accordance with the invention, instead of contouring the allogeneic bone, the patient recipient site in the native jaw is manipulated to have a shape corresponding to that of the allogeneic bone section.

In an example embodiment of the invention, the manipulation of the recipient site 10 involves the preparation of a cylindrical docking area or seat 12 formed transversely into the side of the recipient side 10 in which a cylindrical section of allogeneic bone of standardized diameter can be placed. Recipient sites may be of varying size. Therefore, a plurality of standardized allogeneic bone diameters can be contemplated and prepared. For example, the diameter of the graft may range from about 3 mm to 20 mm. Moreover, the height or thickness of the graft may range from about 2 mm to 10 mm. As noted, the graft material will be allogeneic bone. However, in addition, it may be defined as cortical, cancellous, or corticocancellous. Based on an evaluation of the recipient site, a suitable diameter of allogeneic bone section can be selected and the preparation of the recipient site can be completed using a circular ended cutting burr of a fixed and known diameter. The proposed circular bur has a flat end cutting surface with peripheral flutes that resemble a starfish. Since the preparation of the cylindrical docking area does not need to be more than 1 to 2 mm deep, flutes or a distinct tapered leading edge is not necessary for the drill bit, and a circular burr as aforementioned may be used.

As will be appreciated, a grafting procedure utilizing allogeneic bone grafts for jaw volume augmentation will become far more efficient where the recipient sites can be formed to one of a prescribed number of sizes. Moreover, by standardizing the recipient site to one of a limited number of prescribed diameters, the need for time consuming manipulation of iliac crest in order to maximize recipient jaw contact is eliminated.

In the practice of the invention, according to an example embodiment, once the surgical site is evaluated, a standardized bur 18 is utilized to prepare the circular imprint 12 on the jaw bone 14. In an example embodiment of the invention, a surgical hand guide 16 is utilized to stabilize the circular bur 18 during the cut and to assist in giving the recipient site the appropriate angle to maximize contact and to determine the appropriate size. As will be appreciated, the drill guide is desirably used since otherwise, if a rotating flat base bur with small flutes were to contact a hard surface, the bur would spin out of position.

Figure 4:
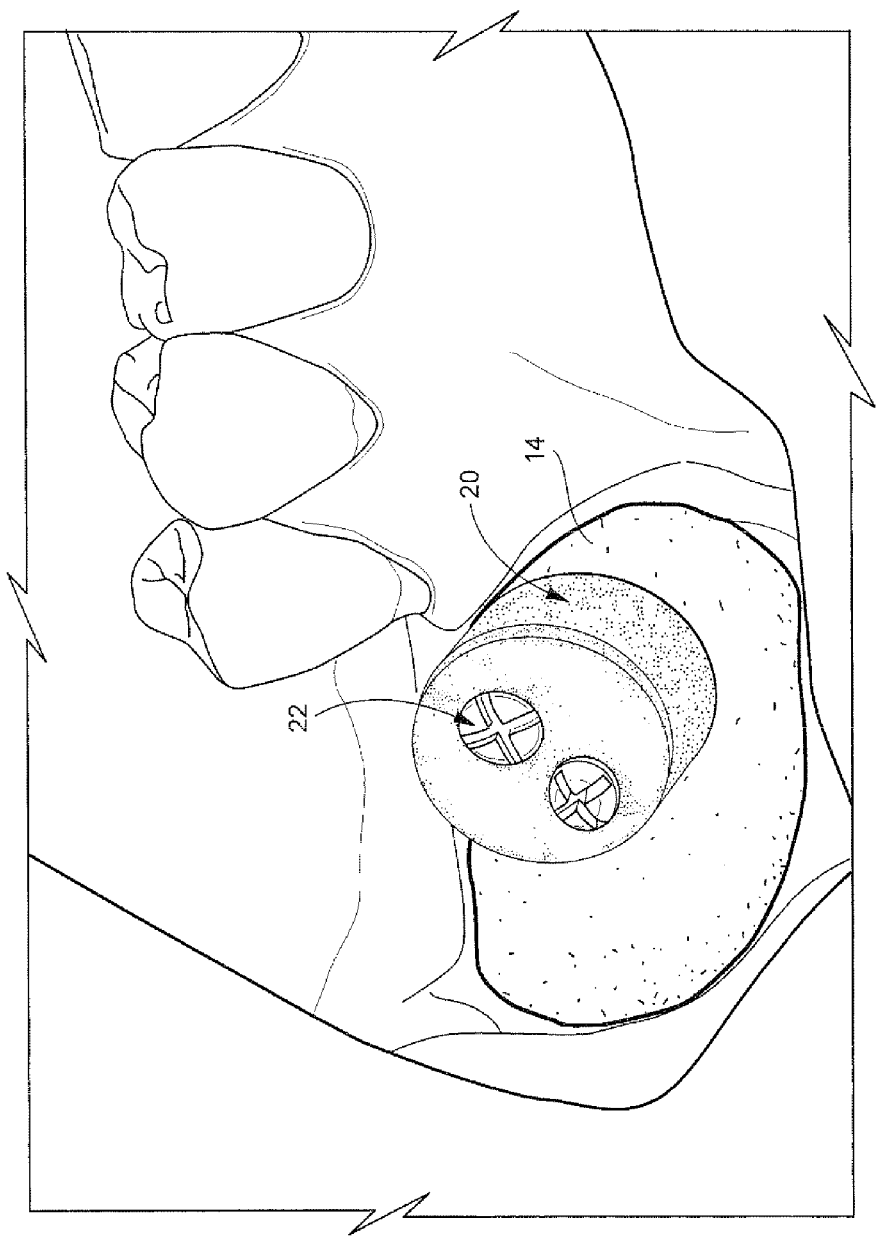
FIG. 4 is a schematic illustration of the patient's recipient site with the allogeneic bone section transversely fixed in place, before soft tissue closure.

Once the imprint is made, the surgeon can then select the corresponding standard bone block 20 from a given stock which matches the diameter and height required to appropriately reconstruct the area which is deficient. Since the recipient site 12 will be a certain diameter and surface contour, a cylindrical block of allogeneic iliac crest can be prepared with that same diameter to fit in the prepared site. The cylindrical block will be fixated with screws 22 as shown in FIG. 4, followed by soft tissue closure and the procedure is complete. As will be appreciated, desirable compression of bone from the graft to the native jaw will come from the screw fixation. As currently proposed, the bone grafting procedure utilizes KLS 1.5 mm by 10 mm screws with associated drill bit for fixation of the bone graft.

As will be appreciated, the new procedure eliminates the need for any interface manipulation of the section of allogeneic bone, thus reducing the surgical time a patient must sustain. The reduction in surgical time would generally be expected to lead to a reduction in post-operative complications and morbidity associated with surgical procedures of the jaw.

In addition to the efficiency of the procedure, due to the standardization of multiple aspects of the grafting procedure, grafting using cylindrical allogeneic blocks will appeal to more dental practitioners who may have been reluctant to complete the procedure in the past due to its complexity.

The invention may also be embodied in a surgical kit including circular burs or drill bits 18 of varying diameter for recipient site preparation, a surgical hand guide 16, and multiple units of cylindrical allogeneic bone 20 with diameters to match the diameters of the respective recipient sites to be formed with the circular drill bits. As noted above, screws 22 and an associated drill bit for fixation of the bone graft are used to complete the procedure. Thus, the kit may also distribute such screws 22 and the associated drill bit (not shown).

Drill guides of various designs are commonly used in maxillofacial fixation systems, e.g., for guiding drills for plate fixation. Such drill guides are conventionally provided for elongated fluted drill bits and to be engaged with the holes in the fixation plates to be secured in place, whereas the drill guide provided in accordance with an example embodiments of the invention has a through bore to accommodate the circular burr 18 and a distal end adapted to engage the natural bone of the jaw 14 rather than engage the bore of a plate.

Although circular burs are illustrated in FIG. 2 according to an example embodiment of the invention, as an alternative, a power-driven osteotome tool or other drill set may be used to form the recipient site, particularly if the graft is to be disposed in a deeper bore. A drill set for forming a bore of prescribed shape and diameter is disclosed for example in U.S. Pat. No. 7,247,020. It will be appreciated that a drill set of the type disclosed in '020 patent or a sub-set thereof may be used to form a suitable recipient site shape corresponding to the cylindrical, or other shaped allogeneic bone section. In addition, or in the alternative, a combination of drill bits and expanders may be used to form a recipient site of suitable diameter and depth to accommodate the allogeneic bone section. Reference is made in this regard to U.S. Pat. Nos. 6,899,715 and 7,241,144, the disclosures of each of which are incorporated herein by this reference.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of fixating allogeneic bone to an area of deficient bone in the jaws comprising:
    exposing the area of deficient bone by incising and retracting soft tissue;
    selecting a drill bit comprising a circular bur with a flat face cutting surface and having a diameter corresponding to the area of deficient bone to receive donor bone;
    selecting a drill guide having a through bore corresponding to the diameter of the selected drill bit;
    directing the selected drill bit through the bore of the drill guide;
    engaging a distal end of the drill guide against a side of the exposed area of deficient bone;
    contacting the selected drill bit with the side of the exposed area of deficient bone and operating rotation of the selected drill bit to form a generally cylindrical seat transversely into the side of the deficient bone for receiving the donor bone;
    selecting a section of donor bone having a generally cylindrical shape and circular cross-section corresponding to said formed seat;
    fixating the donor bone to the formed seat with at least one screw; and
    closing the soft tissue to cover the previously exposed area of deficient bone.

2. A method of fixating allogeneic bone as in claim 1, wherein the cylindrical seat has a depth of 1 to 2 mm.

3. A method of fixating allogeneic bone as in claim 1, wherein said selecting said donor bone comprises selecting a section of one of cortical, cancellous, and corticocancellous bone.

4. A method of fixating allogeneic bone as in claim 1, wherein said selected section of donor bone has a diameter of between 3 mm and 20 mm.

5. A method of fixating allogeneic bone as in claim 1, wherein said selected section of donor bone has a height or thickness of between 2 mm and 10 mm.

* * * * *